United States Patent [19]

Grant et al.

[11] Patent Number: 4,489,239
[45] Date of Patent: Dec. 18, 1984

[54] PORTABLE REMOTE LASER SENSOR FOR METHANE LEAK DETECTION

[75] Inventors: William B. Grant, Altadena; E. David Hinkley, Jr., Glendora, both of Calif.

[73] Assignee: The United States of America as represented by the Administrator of the National Aeronautics and Space Administration, Washington, D.C.

[21] Appl. No.: 423,016

[22] Filed: Sep. 24, 1982

[51] Int. Cl.³ .............................................. G01J 1/00
[52] U.S. Cl. ..................................... 250/339; 250/343
[58] Field of Search ................... 250/338 R, 339, 343; 356/437, 414

[56] References Cited

U.S. PATENT DOCUMENTS

| | | | |
|---|---|---|---|
| 3,788,742 | 1/1974 | Garbuny | 356/5 |
| 3,793,525 | 2/1974 | Burch et al. | 250/343 |
| 3,832,548 | 8/1974 | Wallack | 250/343 |
| 4,059,356 | 11/1977 | Kebabian | 250/343 |
| 4,154,529 | 5/1979 | Dyott | 356/28 |
| 4,263,511 | 4/1981 | Hirschberg | 250/343 |
| 4,426,640 | 1/1984 | Becconsall et al. | 250/339 |

OTHER PUBLICATIONS

Gerritsen, H. J., "Methane Gas Detection Using a Laser," published in SME Transactions, Dec., 1966.
Kucerovsky, Z., et al., "Characteristics of a Laser System for Atmospheric Absorption and Air Pollution Experiments," published in the Journal of Applied Meteorology, Dec., 1973, vol. 12, pp. 1387-1392.
Byer, Robert L., et al., "Pollutant Detection by Absorption Using Mie Scattering and Topographical Targest as Retro-Reflectors," published in Applied Optics, Jul., 1973, vol. 12, No. 7, pp. 1496-1505.
Henningsen, T., et al., "Remote Detection of CO by Parametric Tunable Laser," published in Applied Physics Letters, Mar. 1, 1974, vol. 24, No. 5.

Primary Examiner—Janice A. Howell
Attorney, Agent, or Firm—Paul F. McCaul; Thomas H. Jones; John R. Manning

[57] ABSTRACT

A portable laser system for remote detection of methane gas leaks and concentrations is disclosed. The system transmitter includes first and second lasers, tuned respectively to a wavelength coincident with a strong absorption line of methane and a reference wavelength which is weakly absorbed by methane gas. The lasers are aimed at a topographical target along a system axis and the beams successively interrupted by a chopper wheel.

The system receiver includes a spherical mirror for collecting the reflected laser radiation and focusing the collected radiation through a narrowband optical filter onto an optial detector. The filter is tuned to the wavelength of the two lasers, and rejects background noise to substantially improve the signal-to-noise ratio of the detector. The output of the optical detector is processed by a lock-in detector synchronized to the chopper, and which measures the difference between the first wavelength signal and the reference wavelength signal.

21 Claims, 4 Drawing Figures

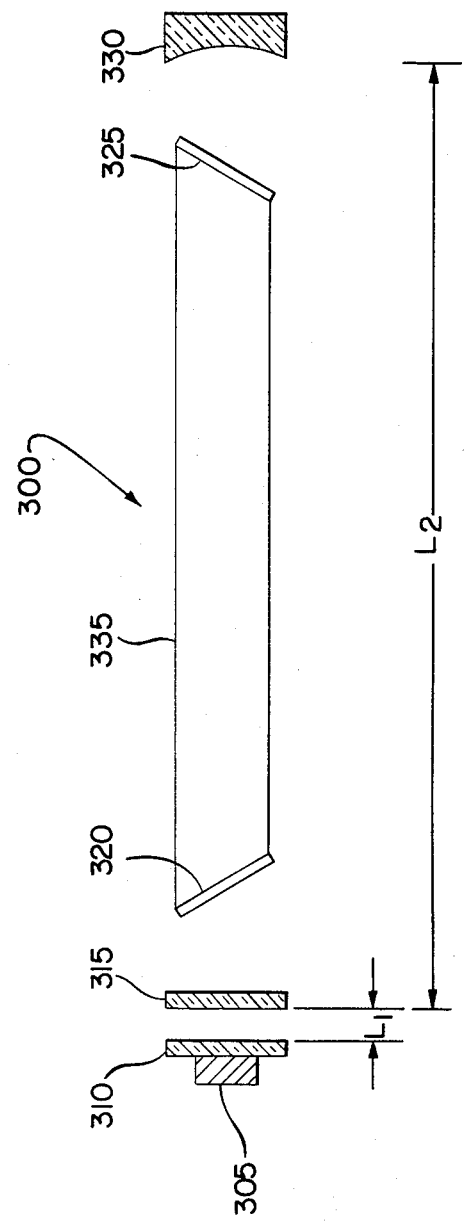

PORTABLE REMOTE LASER SENSOR FOR METHANE LEAK DETECTION

BACKGROUND OF THE INVENTION

1. Field of the Invention

The field of the present invention is gas detection apparatus, and, more particularly, laser apparatus for methane gas detection.

2. Description of the Prior Art

Gas detection systems utilizing lasers tuned to one of the natural absorption lines of the gas molecular species to be detected have been the subject of discussion in the literature. Exemplary of the prior art is the gas monitoring system described in U.S. Pat. No. 3,788,742 ("Garbuny"). This system includes a laser tuned to a wavelength coincident with a natural absorption line of the gas molecular species to be detected. The apparatus is not directed specifically to methane gas, but purports to be tunable and applicable to a range of gas molecular species. A detector is phase locked to the laser assembly by a lock-in amplifier.

The paper "Methane Gas Detection Using a Laser," by H.J. Gerritsen, published in SME Transactions, Dec. 1966, describes a gas detection system utilizing a helium neon laser.

U.S. Pat. Nos. 3,793,525 and 3,832,548 disclose synchronous detection of light beams which have passed through gas samples being analyzed by receivers remote from the transmitter.

The paper "Characteristics of a Laser System for Atmospheric Absorption and Air Pollution Experiments" by Z. Kucerovsky, E. Braunen, K. C. Paulekat and D. G. Rumbold, published in the Journal of Applied Meteorology in Dec. 1973, Volume 12, pp. 1387-1392, discusses a double-beam laser transmitter and receiver system for measuring the concentration of methane in the atmosphere and detection of methane point leaks.

The paper "Pollutant Detection By Absorption Using Mie Scattering and Topographical Targets as Retroreflectors," by Robert L. Byer and Max Garbuny, published in *Applied Optics*, Volume 12, No. 7, pp. 1496-1505, July, 1973, discusses pollution detection using backscattered laser radiation.

The paper "Remote Detection of CO by Parametric Tunable Laser", by T. Henningsen and M. Garbuny, published in *Applied Physics Letters*, Vol. 24, No. 5, Mar. 1, 1974, discusses a transmitter-receiver system for remote detection of carbon monoxide by using topographical features or atmospheric aerosol as the backscattering means.

Insofar as is known, however, the prior art research and development activities have not resulted in any practical, easily portable single-ended methane leak detectors employing low power lasers.

SUMMARY OF THE INVENTION

The present invention includes a pair of helium-neon gas lasers, operating continuously at wavelengths of 3.3922 $\mu$m and 3.3911 $\mu$m, respectively. The two laser beams are chopped by a chopper wheel operating at 2 KHz, and are directed at the area in which gas detection is to occur. The laser radiation reflected by topographical targets is collected by a spherical mirror and imaged through a narrow band optical filter onto an InSb optical detector cooled to 77K. The optical filter is centered at 3.4 $\mu$m, and filters out thermal blackbody and solar background noise, resulting in a substantial improvement in the signal-to-noise ratio of the optical detector.

The amplified output of the optical detector is coupled to a lock-in (phase-sensitive) detector which measures the difference between two signals 180° out of phase. This detector can be used to measure the signal from either laser wavelength, or the difference between the two signals. The lock-in detector is synchronized to the chopper.

Methane concentration is measured using the differential absorption lidar (DIAL) technique. As a particular area is scanned for leaks, the laser is pointed at convenient topographic targets within the system's range, about 25 meters. A portion of the backscattered radiation is collected by the spherical mirror and focused onto the optical detector. The presence of the methane is detected when there is much stronger absorption at the signal wavelength (3.3922 $\mu$m) than at the reference wavelength. The concentrationpathlength product of the methane is given by the log ratio of the signals at the two wavelengths.

Other advantages and features are disclosed.

BRIEF DESCRIPTION OF THE DRAWINGS

FIG. 4 illustrates an alternate embodiment of the laser, adapted to generate a laser beam at two frequencies.

DETAILED DESCRIPTION OF THE PREFERRED EMBODIMENT

Figure 1:
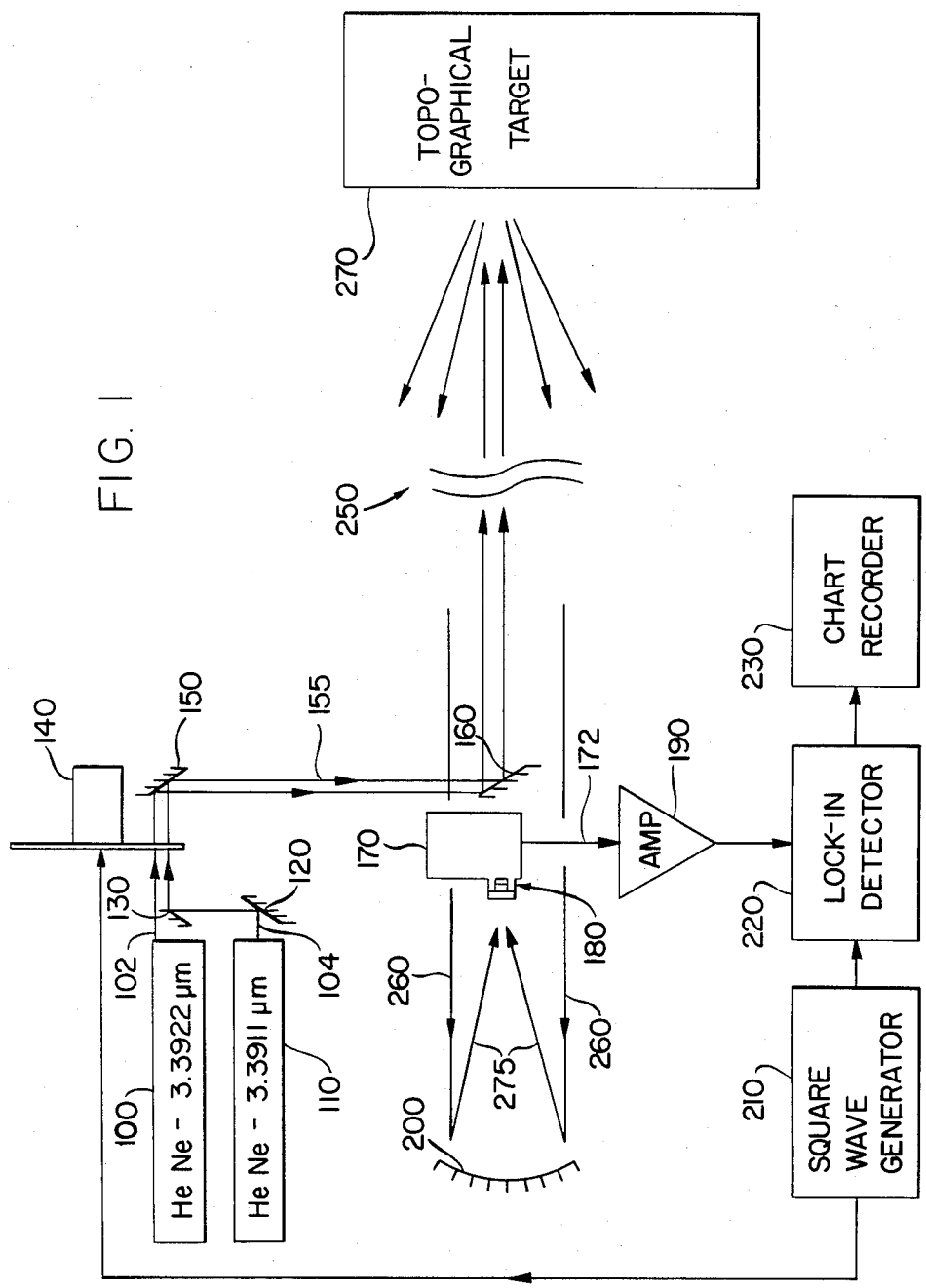
FIG. 1 is a block diagram of the preferred embodiment of the present invention.

The present invention comprises a novel portable methane gas detection system employing lasers. The following description of the invention is provided to enable any person skilled in the art to make and use the invention, and sets forth the best mode contemplated by the inventors of carrying out their invention. Various modifications to the preferred embodiment will be readily apparent to those skilled in the art, and the generic principles of the invention disclosed herein may be applied to other embodiments. Thus, the present invention is not intended to be limited to the embodiment shown, but is to be accorded the widest scope consistent with the principles and novel features disclosed herein.

SPECTROSCOPY OF METHANE

The spectrum of methane ($CH_4$) measured in low resolution has shown that $CH_4$ has two spectral regions with strong features from 1250 to 1370 $cm^{-1}$ (8.0 to 7.3 $\mu$m) and 2900 to 3100 $cm^{-1}$ (3.5 to 3.2 $\mu$m). In addition, there is a weaker overtone band near 6020 $cm^{-1}$ (1.66 $\mu$m). While the strengths of the first two bands are similar, lasers are, at this time, more highly developed in the 3-$\mu$m region. Also, solar radiation decreases rapidly beyond 3 $\mu$m, and the Earth's blackbody radiation increases from 4 to 10 $\mu$m, so the 3-$\mu$m region has a minimum of interference from background radiation.

DIFFERENTIAL ABSORPTION TECHNIQUE

Perhaps the most sensitive way to remotely measure gases in the lower atmosphere with lasers is with the differential absorption technique. In the preferred embodiment, reflected radiation at one laser wavelength at which the gas of interest absorbs strongly is used to detect that gas. The reflected radiation at a second wavelength at which the gas absorbs weakly is used for reference purposes to eliminate other variables. A ratio of the intensity of the radiation at the two wavelengths, suitably corrected for transmitted power and target distance, is used to determine gas concentrations using Beer's law, for the case of a plume in the presence of a background or ambient concentration:

$$cl + CR = \frac{-1}{2\Delta\alpha}\left\{\ln\left(\frac{I}{I_o}\right) - \ln\left(\frac{I'}{I_o'}\right)\right\}, \quad \text{Eq. 1}$$

where
- c is the concentration of gas in the plume (atm or, equivantly, ppm)
- l is the diameter of the plume (cm)
- C is the ambient concentration of the gas (atm)
- R is the distance to the target (cm)
- $\Delta\alpha$ is the differential absorption coefficient (atm$^{-1}$ cm$^{-1}$)
- I(') is the received power for the on (off) wavelength (W)
- and $I_{o(o')}$ is the transmitted power for the on (off) wavelength (W).

In order to use Equation 1 directly with one radiation detector, the two laser beams can be chopped 90° out of phase and two phase-synchronous detectors used to analyze the reflected radiation signals. Alternatively, the beams can be chopped 180° out of phase and blocked successively and one phase-synchronous detector used. For both of these methods, ratios of the two signals are formed to determine the methane concentration-pathlength product.

Another way to use the system is to chop the beams 180° out of phase and detect the reflected radiation at both wavelengths with one phase-synchronous detector and take the difference between the detected signal intensities at the two wavelengths. The signal at the "on" wavelength (i.e., the strongly absorbed wavelength) has the form:

$$I = \frac{I_o A \rho \eta \exp(-2\alpha(cl + CR))}{\pi R^2} \quad \text{Eq. 2}$$

where
- A is the receiver area (cm$^2$)
- $\rho$ is the reflectance of the target
and
- $\eta$ is the receiver efficiency.

The signal at the "off" wavelength (i.e., the weakly absorbed wavelength) can be formed from Eq. 2 by adding factors or "primes" to the variables that change with wavelength. The difference signal is then:

$$I - I' = \frac{A\eta}{\pi R^2}[\rho \exp(-2\alpha(cl + CR)) - \rho' \exp(-2\alpha'(cl + CR))]. \quad \text{Eq. 3}$$

For the case where $\rho = \rho'$, it becomes $$I - I' = \frac{A\eta\rho}{\pi R^2}(\exp(-2\alpha(Cl + CR)) - \exp(-2\alpha'(cl + CR))). \quad \text{Eq. 4}$$

And for the case where $2\alpha(cl + CR) << 1$, it becomes $$I - I' \approx \frac{-A\eta\rho\Delta\alpha}{\pi R^2}(cl + CR), \quad \text{(Eq. 5)}$$

which is directly proportional to the concentration and thus represents a potentially very useful technique for detecting small leaks. However, since the ratio of $\rho$ to $\rho'$ may vary with the target materials, this approach could lead to scanning-system problems, as discussed below. This approximation is valid for concentrationpathlengths less than about 100 ppm-m, for which the error is less than 5% The system becomes simpler in this case because only one, and not two, signal processing channels is required, since a difference, rather than a ratio, is measured.

In the 3-$\mu$m region, the HeNe laser at 2947.9 cm$^{-1}$ (3.3922-$\mu$vacuum wavelength or 3.3913 $\mu$m in air) has a strong overlap with a methane line (absorption coefficient $(\alpha) \approx 8.8$ cm$^{-1}$atm$^{-1}$). In addition, the HeNe laser can be made to lase at 2948.9 cm$^{-1}$ ($\lambda$ vacuum = 3.3911 $\mu$m) with the addition of an intracavity cell containing CH$_4$ to quench the dominant line at 2947.9 cm$^{-1}$. The HeNe laser has been used by others in several laboratory and field demonstrations of the measurement of CH$_4$. Other lasers that have been used for remote measurement of CH$_4$ on weaker lines include the OPO laser, the DF laser, the Er:YAG laser, and the diode laser.

THE PREFERRED EMBODIMENT

A block diagram of the preferred embodiment of the invention is shown in FIG. 1, and the components and their parameters are listed in Table I. Laser beams 102 and 104 generated by HeNe lasers 100 and 110 respectively for the "on" and "off" wavelengths are made parallel and nearly colinear by means of a pair of mirrors 130 and 120 which redirect beam 104. The beams are separated just enough so that they can be chopped 180° out of phase by the small-aperture (5 mm) chopper 140 that operates at 2 kHz. Two additional mirrors 150 and 160 are used to redirect both beams to be substantially coaxial with the receiver axis.

Backscattered radiation from topographic target 270 is collected by a 37-cm diameter spherical receiver mirror 200 and directed through optical narrowband filter 180 to InSb detector 170. Both optical detector 170 and filter 180 are cooled to 77K to minimize noise. Filter 180 reduces background radiation by a factor of four. The detected radiation signal 172 is amplified by amplifier 190 and processed by lock-in (phase-synchronous) detector 220, synchronized to operation of the chopper 140.

The helium-neon (HeNe) lasers 100 and 110 operate continuously (CW) and emit a beam with a divergence of about 1 mrad (expands to 1 m in 1 km). The Spectra Physics Model 120 laser 100 emits 1.6 mW at 3.3922 $\mu$m ($\alpha$CH$_4 \approx 8.8$ cm$^{-1}$atm$^{-1}$); the Spectra Physics Model 124B laser 110 emits 2.2 mW at 3.3911 $\mu$m ($\alpha$CH$_4 \approx 0.8$ cm$^{-1}$atm$^{-1}$). The chopper wheel is operated at 2 kHz, which is high enough to reduce much of the mechanical (1/f) noise occurring at lower frequencies.

TABLE 1

| Transmitter | |
|---|---|
| HeNe Laser (2) | Spectra Physics Models 120 and 124B |
| Input power | 50–100 W |
| Emitted power | 1.5 mW |
| Beam divergence | 1 mrad |
| Wavelength - "on" | 3.3922 μm (vacuum) |
| Wavelength - "off" | 3.3911 μm (vacuum) |
| (intracavity cell containing CH$_4$ used with "off" wavelength laser) | |
| Chopper | Princeton Applied Research, Model 125A |
| Chopper frequency | 2kHz |
| Receiver | |
| Mirror 200 | |
| Diameter | 14.5" (36.8 cm) |
| Focal length | 34.5" (87.6 cm) |
| Surface | spherical |
| Coating | aluminum with SiO$_2$ overcoat |
| Optical Detector | Judson Infrared |
| Material | InSb |
| D* | ~10$^{11}$ cm Hz$^{\frac{1}{2}}$ W$^{-1}$ |
| Diameter | 2 mm |
| Temperature | 77 K |
| Optical Filter | (Optical Coating Laboratory, Inc.) |
| Bandwidth (half power) | 4.2% |
| Peak transmission | 70% |
| Temperature | 77 K |
| System optical efficiency | 0.2 |
| Signal processing electronics | |
| Phase-sensitive (lock-in) detector | |
| Princeton Applied Research | |
| (sensitive from 1 μV to 500 mV) | |
| Dual-channel chart recorder | |

Chopper 140 includes a five-inch wheel of an opaque material having slots therein at approximately one-quarter-inch intervals for passing light therethrough. The chopper wheel is arranged and disposed such that the "on" and "off" wavelengths are alternatively passed through the chopper wheel. Thus, when the "on" wavelength is passed by the chopper wheel during a first portion of the chopper wheel cycle, the "off" wavelength is not passed, i.e., it is chopped. And when the "on" wavelength is chopped during a second portion of the chopper cycle, the "off" wavelength is passed by the chopper.

The output from detector 170 will include both a background-noise component as well as a data component representing the intensity of the reflected laser radiation. In general, the background-noise component will be larger than the data component, but will be relatively slow varying with respect to time, and may therefore be considered a dc component.

Detector 220 is adapted to integrate the amplified signal output from detector 170 over each chopper portion, and to store the integrated value. Thus, for the first portion of the chopper wheel when only the "on" wavelength is transmitted, the detector 220 integrates both the background noise and data components, resulting in a first summed value. This value is stored by the detector. During the second portion of the chopper cycle when only the "off" wavelength is passed, the background noise and data components are integrated, resulting in a second summed signal. Detector 220 is adapted to form a differential value representing the difference between the first summed signal and the second summed signal. The background noise components are assumed to cancel out, since it is assumed that the background noise level is the same at the "on" wavelength as at the "off" wavelength. Hence, the differential value comprises the difference between the integrated data signal from the first wavelength and the integrated data signal for the "off" wavelength.

MEASUREMENT OF SYSTEM SIGNAL AND NOISE

The signal power measured by a laser system is given by Equation 2. For the disclosed system, the following values of the parameters are assumed:

$I_o = 1.5$ mW
$\rho \approx 0.07$
$A \approx 0.095$ m$^2$
$\eta \approx 0.2$
$R = 15$ m
$\alpha = 8.8$ cm$^{-1}$ atm$^{-1}$
$C = 1.6 \cdot 10^{-6}$ atm
and
$cl = 0$.

Putting these values in Eq. 2 yields a value of $2.7 \cdot 10^{-9}$ W.

The detector noise equivalent power (NEP) is given as $$NEP = \frac{A_d^{1/2} \tau^{-1/2}}{D^*} \text{ (watts)} \qquad \text{Eq. 6}$$

where $A_d$ is the area of the detector (cm$^2$)
$\tau$ is the integration time
and
D* is the detectivity of the detector (cm Hz$^{\frac{1}{2}}$W$^{-1}$)

For the preferred embodiment, $A_d = 0.03$ cm$^2$, $\tau = 1$ sec and $D^* = 10^{11}$ cm Hz$^{\frac{1}{2}}$W$^{-1}$. With these values, Eq. 6 yields a detector NEP of $3 \cdot 10^{13}$ W.

Even with the narrow band filter, solar and thermal background radiation also contribute to the system noise. At 3.4 μm, the combined background radiation is about $10^{-4}$ W/(cm$^2$ sr μm). For the disclosed system, this calculates to be $1.33 \cdot 10^{-13}$ W.

A variety of targets have been used to empirically check the measurement as a function of material and reflectivity. Vegetation gave about the lowest reflected signal intensity, asphalt an intermediate signal, wood and gravel a fairly high signal, and crumpled aluminum a signal 20 times that for asphalt. The reflectivities of most natural non-vegetation targets were within a factor of 3 of each other.

The chopper frequency has been varied experimentally from 360 to 2400 Hz, and the system signal-to-noise ratio was determined for each setting for one laser wavelength. The laser was pointed at a pine wall target 20 m away, and an integration time of 0.1 sec was used. The S/N increased from 11 at 360 Hz to 22 at 2400 Hz in a monotonic fashion.

As noted above, differential spectral reflectance changes, i.e., changes in the relative reflectance at two wavelengths, can be a serious source of noise for laser systems that use topographic targets. The "on" and "off" laser wavelengths of the preferred embodiment are approximately 1 cm$^{-1}$ apart. For radiation having wavelengths between 3 and 4 μm, some targets, such as paint, may have a factor of four change in reflectance, while others may have no change. In other words, there can be up to a 400% change in reflectance in an 833 cm$^{-1}$ spectral interval. This corresponds to a maximum of about 0.5% for the 1 cm$^{-1}$ separation in wavelength of the two HeNe laser lines used for methane detection. Usually, however, the effect would be considerably less, probably about 0.05%, which corresponds to a methane measurement error of 0.3 ppm-m.

Another factor which affects the measurement accuracy is receiver-to-target distance variation. The image plane of a receiver mirror varies with the distance to the object by the relation:

$$\frac{1}{f} = \frac{1}{i} + \frac{1}{o} \qquad \text{Eq. 7}$$

where
f is the focal length
i is the mirror to image distance,
and
o is the mirror to object (target) distance.

For a 30-cm-diameter spherical mirror, with a focal length of 105 cm, the change in the image plane is quite noticeable at short receiver-to-target distances. Some values are given in Table II:

TABLE II

| Target Distance (o) (m) | Image Plane (i) (cm) |
|---|---|
| 10 | 117.3 |
| 30 | 108.8 |
| 60 | 106.9 |
| 100 | 106.1 |
| ∞ | 105 |

Figure 2:
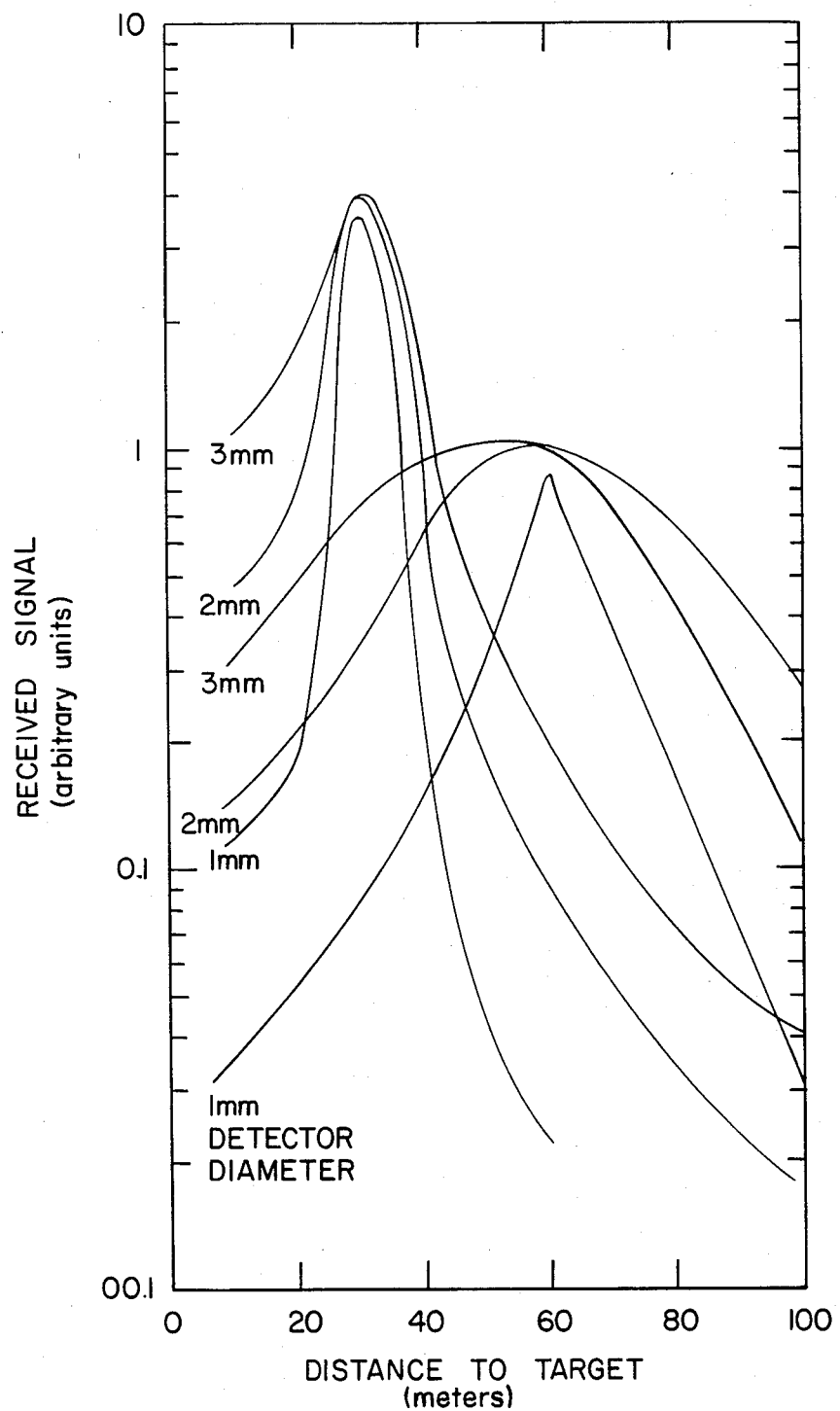
FIG. 2 is a graphical illustration of the calculated received signal of the disclosed system as a function of the distance to the target for two focal positions of three detectors.

This variation in the position of the image plane as a function of target distance has the effect of reducing the detected signal for target distances other than that for which the detector is set. Essentially, the image is blurred over a larger diameter as the range changes. There is some mitigation of this effect by the $1/R^2$ increase in signal from a topographic target as the range (R) is decreased. An example of this effect is shown in FIG. 2, which plots the calculated received signal as a function of distance to the target for two focal positions of three different sizes of detectors. The effect is less pronounced for larger detectors, since the noise of a detector due to blackbody radiation normally increases linearly with the diameter. A 2-mm diameter detector would be superior to a 1-mm diameter detector for the range 44–84 m, while a 3-mm diameter detector would be better if an extended range were to be used without changing the detector position. If a limited set of ranges were to be used, it is better to change the detector position than go to a larger detector.

Many hydrocarbons have strong, broad absorption bands somewhere in the specral wavelength region of 3.2 to 3.5 μm. This arises from the C-H stretch vibrational mode. Using the low resolution spectra available (e.g., in the Sadtler Spectral Atlas), it is difficult to tell whether particular hydrocarbons would interfere with a measurement of methane. In order to interfere, the gas would have to have a differential absorption for the two wavelengths chosen for the methane measurement. By choosing two lines close together as with the HeNe laser, the interference is minimized.

To assess this interference effect, the absorption coefficients of several hydrocarbons were measured at the wavelengths chosen to detect methane. The results of the measurement are given in Table III. Some gases, such as butane and propylene, have small differential absorption coefficients at the two HeNe wavelengths (acetylene and benzene have no absorption at 3.39 μm), while others, such as ethane, isobutane and propane have differential absorption coefficients that are large enough to cause noticeable interference—or to allow these gases themselves to be detected near their source, e.g., leaking propane near a propane storage tank. The sign of the differential absorption coefficient changes for some gases. Thus, in a mixture of hydrocarbons, such as gasoline, the combined differential absorption-coefficient might be quite small. However, automobile exhaust, which can contain up to 10% $CH_4$ of the total hydrocarbon, which is only a few percent of the gaseous emissions, might give a measurable signal.

TABLE III

| Gas | $\alpha_{3.3922\ \mu m}$ (atm$^{-1}$cm$^{-1}$) | $\alpha_{3.3911\ \mu m}$ (atm$^{-1}$cm$^{-1}$) | $\Delta\alpha$ (atm$^{-1}$cm$^{-1}$) |
|---|---|---|---|
| Methane | 8.8 | 0.8 ± 0.3 | +8.0 ± 0.3 |
| Butane | 10.9 ± 0.4 | 11.0 ± 0.4 | −0.1 ± 0.6 |
| Ethane | 3.69 ± 0.19 | 2.69 ± 0.08 | +1.0 ± 0.2 |
| Isobutane | 11.1 ± 0.2 | 13.0 ± 0.4 | −1.9 ± 0.4 |
| Propane | 8.27 ± 0.04 | 7.41 ± 0.03 | +0.86 ± 0.86 |
| Propylene | 2.23 ± 0.06 | 2.40 ± 0.02 | −0.17 ± 0.06 |

Since ethane, isobutane and propane have fairly substantial differential absorption coefficients for the two wavelengths selected for the preferred embodiment, the system could therefore be used to check for leaks in containers of these gases.

The disclosed system may be mounted on a wheeled cart, having a table for mounting the optical components. The table preferably is of Kevlar-coated, aluminum honeycomb material, with a very low thermal expansion coefficient. The table can be tilted ±10°. Ten-inch-diameter pneumatic wheels isolate the system from vibrations as it is transported. A gasolinepowered electrical generator can be used to supply electrial power. The system requires only 300 watts.

A rigid 1.5-inch-diameter pole with micrometerscrew adjusts is used to mount the two mirrors 150, 160 which bring the two laser beams into near coincidence with each other. The receiver mirror has tapered edges to reduce the weight to 16 pounds, a 2-inch (5-cm) hole in the center, and a focal length of 34.5 inches (88 cm).

Global background methane does not, in general, affect the methane leak measurements, as long as the background methane is uniformly mixed and the distance to the target does not vary. If the distance to the target varies, then there will be an additional change in the differential absorption of about 0.25% per meter change, or a 1.6-ppm-m change (based on a global background concentration of 1.6 ppm)

Tests have been performed to define useful range, detection limits, spectral interferences, and variations in target reflectance. The tests were conducted at a sanitary landfill and at several sites along an underground gas distribution system where methane was venting into the atmosphere. At a range of 13 m, the detection limit for methane (above its global concentration of 1.6 ppm) was estimated to be 3 ppm for a 1-m pathlength. The system also performed well in the presence of high concentration-pathlengths.

As shown in Eqs. 6 and 7, the signal-to-noise ratio depends on several factors. For a given system, the range-dependence and time-dependence factors are most important. Thus, the sensitivity to methane increases (detection limit decreases) as the range decreases, up to some point a few meters in front of the system. The sensitivity also increases as the integration time increases, but increasing the time constant decreases the rate at which the system can be scanned when searching for leaks.

Figure 3:
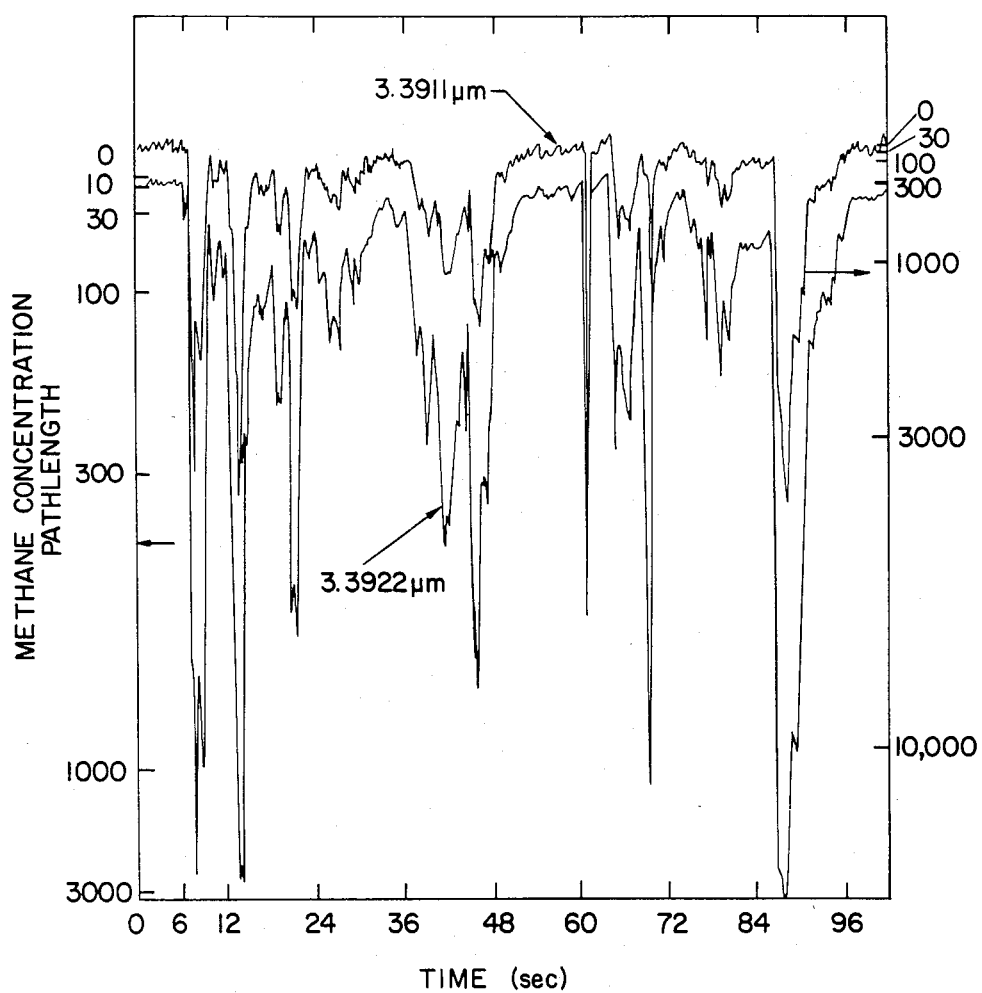
FIG. 3 is a graphical illustration showing the time-varying methane absorption characteristics.

It is understood through laboratory tests that the time-varying behavior of escaping natural gas is an excellent indication of its presence. In one set of tests, the laboratory supply of natural gas was brought out to a point a few inches below the system laser beams. The system was aimed at an asphalt road about 13 meters away. The time constant of the phasesynchronous detector was set at 0.03 seconds. When the gas blew into the beams, the signal for both wavelengths decreased, as is shown in FIG. 3, which plots the timevarying methane absorption values as a function of time. The signal at both wavelengths varies, as expected from Equation 2, even though the absorption coefficients vary by a factor of 11. The exponential function varies much more rapidly for a given change in the exponent for small values of the exponent, so that the ratio of the measured signal intensities are less than a factor of 11.

One HeNe laser can be designed to generate the two wavelengths required for methane detection. A Fabry-Perot interferometer replaces the rear mirror. In general, the Fabry-Perot interferometer will transmit (or reflect) only those wavelengths for which its two mirror spacing satisfies the expression:

$$\lambda = 2d/m \quad \text{Eq. 8}$$

where $\lambda$ is the wavelength d is the mirror spacing and m is an integer.

If one mirror of the interferometer can be moved, the spacing, d, can be changed so that the other wavelength is favored. The mirror spacing should be such that Eq. 8 is satisfied for one wavelength but off by a half wavelength for the other wavelengths. The smallest separation for which this occurs is given by:

$$\Delta \nu = 1/4d \quad \text{Eq. 9}$$

where $\Delta \nu$ is the separation in wavenumbers ($cm^{-1}$) between the two wavelengths.

For the two HeNe wavelengths of the preferred embodiment, the separation is approximately 0.9 $cm^{-1}$, giving a minimum separation of about 2.8 mm. The mirror separation would have to change by half a wavelength (1.72 $\mu$m) to allow the other wavelength to be favored.

This can be realized by placing the rear mirror of the Fabry-Perot interferometer on a piezoelectric disc and oscillating it at about 1 kHz, as shown in U.S. Pat. No. 4,059,356. The cavity length of the laser of this patent, however, is limited to 7 in. and included both the wavelength control and plasma tube. This cavity length limited the laser power to 10 $\mu$W, too low to be useful for remote measurements as in the present system. By using a three-mirror cavity as discussed in the paper "Improved Use of Gratings in Tunable Lasers," by J. E. Bjorkholm, T. C. Damen and J. Shaw, published in *Optics Communication*, Vol. 4, p. 283 (1971), the plasma tube can be made long enough to generate 2 mW without limiting the tuning of the laser.

FIG. 4 illustrates a laser having a threemirror cavity which may be used in place of the two HeNe lasers 100, 110 shown in FIG. 1. Lasing conditions would have to be satisfied for each section of the laser, which means that the tuning may be slightly irregular due to the several hundred MHz mode spacing in the long section.

Mirrors 320 and 325 comprise the Brewster angle windows, disposed at the ends of the HeNe plasma tube 335. Mirrors 310 and 315, coated with $CaF_2$ and having a reflectivity of about 90%, comprise the Fabry-Perot interferometer. Mirrors 310 and 315 are separated by a distance $L_1 = 2.78$ mm. Piezoelectric disc 305 is oscillated by a drive oscillator (not shown) of about 1 $\mu$m. Mirror 330 has a reflectivity of about 95%. The length $L_2$ of plasma tube 335 is 40 cm.

Detector 170, when used with the alternate laser arrangement of FIG. 4, is synchronized with the oscillation of mirror 310, since the chopper is no longer necessary.

Plasma tube 335 can be driven with 20 W of electrical power. An invar-stabilized cavity can be used to reduce amplitude instability due to change in cavity length. A cell containing a small amount of methane may also be inserted into the cavity in order to equalize the gain at both laser wavelengths so that equal power is generated at each wavelength.

The collector mirror should be large, lightweight, and preferably off-axis. The mirror used in the present system has a diameter of 14.5 in. (37 cm), and a usable area of 150 in.$^2$ (0.095 m$^2$). This is adequate for 2 mW of laser power and topographic targets out to 15 m.

If a system is to work at ranges as great as 30 m, and since the backscattered signal falls off as the inverse square of the distance, a collector area of up to four times that of the present collector is desirable. (Alternatively, the time-constant of the phasesensitive detector could be increased.)

The collector focal length for use in a hand carried system should be reduced to about 12 in. (30 cm) in order to tightly focus the collected light on the detector. This reduces the effect of changes in distance to the target and allows the transmitted divergence to be as large as 9 mrad (0.5°).

The off-axis requirement arises from the need to look for leaks as close as 3 m from the system. If a detector in a large dewar were at a focal point on an axis in the center of the collector, close-in targets would be obscured. The tip on the dewar should be smalldiameter so that such obscuration can be minimized. In that case, an on-axis collector could be used. With the off-axis collector, a special curve would have to be designed for optimum focusing on a detector for a range of targets from 3 to 30 m. A master surface can then be made and used to generate metal collector replicas. Since the mirror acts more like a "light bucket" rather than an image, the surface quality should be high enough.

As an alternative to a spherical collector lens, a Fresnel lens made of Kel-F could be used (such as, for example, the lens available from Lectric Lites Co., Fort Worth, TX). Since the Fresnel lens is disposed between the optical detector and the topographical target, the losses due to the detector blocking of received radation (20-30%) are eliminated.

A 2-mm-diameter InSb optical detector, cooled with liquid nitrogen to 77K, and preceded by a cooled narrow-band filter is presently understood to be the optimal configuration. Cooling the detector eliminates much of the blackbody radiation associated with higher temperatures and allows the system to be sensitive to backscattered radiation from topographic targets. The dewar need be filled but once a day with liquid nitrogen. The optical filter further reduces background radiation incident on the detector.

Cooling could be accomplished with an expanding-gas cryostat (Joule-Thomson effect). Another approach is to thermoelectrically cool the detector to 190K, which would result in a D* an order of magnitude lower.

For small leaks, only one phase-synchronous detector is required using the difference technique. This can be followed by a device that converts the signal amplitude from the phase-synchronous detector to an audible signal that changes frequency or amplitude with signal strength.

The optical portion of the system weighs between 10 and 15 pounds. The total system weighs about 25 pounds, and draws between 30 and 40 watts of electrical power. This can be supplied from a battery. A lead acid battery that weighs six pounds and supplies 50 watt-hours of power is available.

There has been described herein a system for remote detection of methane gas leaks. The system is adapted for portable use to detect gas leaks in gas pipelines, landfill sites and the like.

What is claimed is:

1. A portable, low wattage system for remotely detecting methane gas concentrations in the atmosphere from radiation reflected from a topographical target, said radiation including thermal and solar-type background noise, including methane-related laser wavelengths to be analyzed, said system comprising:

means for generating a first laser beam at a first wavelength coincident with a natural absorption line of methane gas;

means for generating a second laser beam at a second wavelength which is not a strong absorption line of methane gas;

means for successively interrupting said first and second laser beams;

means for directing said first and second laser beams at a topographical target;

collecting means for focusing a portion of said reflected laser radiation;

narrowband optical filter means centered near said first and second wavelengths for passing said focused radiation, including the wavelengths to be analyzed and for effectively reducing said thermal and solar-type background noise;

optical detector means for detecting the intensity of incident laser radiation and generating a detector signal representative of such intensity;

signal processing means synchronized to the operation of said means for interrupting said laser beams for performing processing of the data from said optical detector to effectively cancel out the background noise while providing an output signal indicative of the relative intensity of said radiation at said first wavelength.

2. The system of claim 1 wherein said first wavelength is about 3.3922 $\mu$m and said means for generating said first wavelength comprises a first Helium Neon laser.

3. The system of claim 1 wherein said first and second wavelengths are within one $cm^{-1}$ (0.001 $\mu$m) of each other.

4. The system of claim 3 wherein said second wavelength is about 3.3911 $\mu$m and said means for generating a second laser beam comprises a second Helium Neon laser.

5. The system of claim 4 wherein a cell containing $CH_4$ is disposed in the optical cavity of said second laser.

6. The system of claim 1 wherein said interrupting means is adapted to interrupt said first and second laser beams 180° out-of-phase, wherein only said first laser beam is passed during a first portion of the cycle of the interrupting means, and only said second laser beam is passed during the succeeding portion of said cycle.

7. The system of claim 6 wherein said signal processing means is adapted to integrate said detector signal over said first portion of said cycle to form a first summed signal and to integrate said detector signal over said second portion of said cycle to form a second summed signal.

8. The system of claim 7 wherein said signal processing means is further adapted to form a difference signal P representative of the difference between said first summed signal and said second summed signal.

9. The system of claim 1 wherein said signal processing means is adapted such that said detector signal is determined, when $2\alpha(cl+CR) \ll 1$, in accordance with the following expression:

$$D \simeq -\frac{A\eta\rho\Delta\alpha}{\pi R^2}(cl + CR),$$

where A is the area ($cm^2$) of the optical detector, $\rho$ is the reflectance of said topographical target, 1 is the optical detector efficiency, $\Delta\alpha$ is the differential absorption coefficient ($atm^{-1} cm^{-1}$), c is the concentration of gas in the methane gas plume (atm or ppm), 1 is the diameter of the plume(cm), C is the ambient concentration of the gas (atm) and R is the distance from the optical detector to the topographical target (cm).

10. The system of claim 1 further comprising cooling means for cooling said optical detector and said optical filter means.

11. The system of claim 10 wherein said cooling means is adapted to cool said detector and said optical filter to about 77K.

12. The system of claim 1 wherein said optical detector means is adapted to detect incident laser radiation having wavelengths from 1 $\mu$m to 4 $\mu$m.

13. The system of claim 1 wherein said collector means is adapted to focus said incident laser radiation at an image plane, and said optical detector means is disposed at said image plane.

14. The system of claim 1 wherein said narrowband filter means is centered at about 3.4 $\mu$m and its power transmission points are at about ±0.07 $\mu$m on each side of said center.

15. The system of claim 1 wherein said collecting means comprises a spherical mirror.

16. The system of claim 15 wherein said optical detector means is disposed between said spherical mirror and said topographical target.

17. The system of claim 1 wherein said collecting means comprises a Fresnel lens means.

18. A portable, low wattage system for detecting methane gas concentrations in the atmosphere from reflected laser radiation which includes methane wavelengths to be analyzed and thermal, solar or room light background noise, said system comprising:

laser means adapted for selectively generating a laser beam at either a first wavelength coincident with a natural absorption line of methane gas or at a second wavelength which is not a strong absorption line of methane gas;

control means coupled to said laser means for alternatively selecting said laser beam at said first wavelength and then said seond wavelength;

means for directing said laser means at a topographical target;

collecting means for focusing a portion of the laser radiation and background noise reflected from said target;

narrowband optical filter means centered near said first wavelength for passing said focused first and second wavelengths of laser radiation and effectively reducing said background noise by a factor of up to four;

optical filter means responsive to the signals passed through said narrowband optical filter means for detecting the intensity of incident laser radiation and generating a detector signal representative of such intensity; and signal processing means synchronized to the operation of said selecting means for processing the data from said optical detector and providing an output signal indicative of the relative intensity of said laser radiation at said first wavelength.

19. The system of claim 18 wherein said laser means includes a plasma cavity having Brewster angle windows and further including a Fabry-Perot interferometer disposed on a piezoelectric disc, said disc being driven by oscillator means, whereby for one position of said disc, the laser produces a laser beam at said first wavelength, and for a second position of said disc means, said laser means produces a laser beam at said second wavelength.

20. The system of claim 19 wherein said signal processing means is synchronized to the operation of said oscillator means.

21. The system of claim 19 wherein the portability of the system results from the system's total weight of around 25 pounds, and the low wattage required by the system is in the area of 40 watts of electrical power, said system further comprising a battery for supplying said wattage to remotely and portably sense methane leaks.

* * * * *